(12) United States Patent
Smith

(10) Patent No.: US 7,666,058 B2
(45) Date of Patent: Feb. 23, 2010

(54) SYNMASTIA COMPRESSION BRA

(76) Inventor: Veronica C. Smith, 999 Marina Way South, Richmond, CA (US) 94804

( * ) Notice: Subject to any disclaimer, the term of this patent is extended or adjusted under 35 U.S.C. 154(b) by 74 days.

(21) Appl. No.: 12/030,187

(22) Filed: Feb. 12, 2008

(65) Prior Publication Data

US 2008/0194178 A1     Aug. 14, 2008

Related U.S. Application Data

(60) Provisional application No. 60/889,882, filed on Feb. 14, 2007.

(51) Int. Cl.
*A41C 3/00*     (2006.01)
(52) U.S. Cl. .................................. 450/8; 450/20; 450/21
(58) Field of Classification Search ............. 450/8, 450/19–21, 23, 39, 40, 60–63, 70–85
See application file for complete search history.

(56) References Cited

U.S. PATENT DOCUMENTS

| | | | | |
|---|---|---|---|---|
| 3,419,895 A * | 12/1968 | Stephensen | ............... | 450/60 |
| 3,491,762 A * | 1/1970 | Simonsen | ................... | 450/60 |
| 3,642,009 A * | 2/1972 | Nobbs | ........................ | 450/60 |
| 3,769,987 A * | 11/1973 | Markowitz | ................ | 450/60 |
| 5,221,227 A * | 6/1993 | Michels | ....................... | 450/1 |
| 5,968,003 A * | 10/1999 | Sisson | ........................ | 602/75 |
| 6,860,789 B2 * | 3/2005 | Bell et al. | ..................... | 450/20 |
| 7,144,294 B2 * | 12/2006 | Bell et al. | ..................... | 450/20 |

* cited by examiner

*Primary Examiner*—Gloria Hale
(74) *Attorney, Agent, or Firm*—David E. Newhouse, Esq.

(57) ABSTRACT

A compression bra for addressing and/or correcting synmastia complications in reconstructive breast surgeries has: (i) a wide, cotton-lined, unidirectional elastic, torso band adjustably encircling a woman's thoracic torso immediately below the inframammary skinfold; (ii) a trapezoidal shaped, sternum compression panel secured at its base to the upper edge of torso band below the inframammary skinfold and at the top by a pair of adjustable over-the-shoulder straps for elastically compressing sternum tissues while restraining, shaping and separating the inside conically rising, side portions of a woman's breasts; (iii) a pair of breast support cups/flaps also fastened to the upper edge of the torso band each similarly secured at the top by an adjustable over-the-shoulder support strap; and (iv) elastic side panels fastened to the breast cup/flaps and the upper edge of the torso band for anchoring the respective shoulder straps of the sternum compression panel and breast cups/flaps supporting, restraining and shaping the outside, conical rising side portions of the woman's breasts.

4 Claims, 6 Drawing Sheets

SYNMASTIA COMPRESSION BRA

RELATED APPLICATIONS

This application relates to U.S. Provisional Patent Application Ser. No. 60/889,882, Confirmation No. 5453 filed 14 Feb. 2007 entitled SYNMASTIA COMPRESSION BRA, which is incorporated herein by reference in its entirety, and claims any and all benefits to which it is entitled thereby.

BACKGROUND OF THE INVENTION

1. Field of the Invention

This invention relates generally to a compression stabilizing, supporting and positioning bra for addressing and/or correcting synmastia complications in reconstructive breast surgeries.

2. Description of the Prior Art

Cosmetic breast surgeries and surgical breast reconstruction following a mastectomy typically require that the newly configured breasts be stably positioned and supported on the underlying tissues postoperatively. In particular, breast implants tend to move postoperatively in the case of breast augmentation and breast reconstructions (See U.S. Pat. No. 5,037,348, F. G. Farino and U.S. Pat. No. 5,098,331, M. W. Corrado). For mastopexy (breast lift) and mammoplasty (breast reduction) procedures, postoperative support and positioning is critical for reshaping the breast.

In more detail, a woman's breasts consist of a framework of connective tissue and a system of glands and ducts that produce milk. Fat makes up the majority of the breast tissue. Behind the breast tissue are the pectoralis muscles. The connective tissues supporting the breasts are skin and ligaments, both of which are somewhat elastic and do stretch. Accordingly, distortions due to postoperative swelling caused by excessive buildup of fluid in the tissues responsive to the surgical incisions, and tissue removal must be addressed, in order to assure that the skin and surgically relocated breast tissues properly reattach to underlying supportive tissue layers for the desired breast configuration.

Synmastia is a rare but severe complication of breast enhancement surgery that can occur when the breast implants are positioned toward the middle of the chest in an effort to provide more cleavage. Synmastia complications are for the most part a result of undue stress lifting the midline tissues from the sternum. For example, the plastic surgeon may deliberately or otherwise disturb the connective and support near the sternum in an effort to bring the augmented breasts closer together. Synmastia can also occur where breast implants are simply too large for a woman's anatomy. It may also occur because of a woman's anatomy and genetic makeup.

In particular, breast implants typically are composed of incompressible but flexible, flowable mediums and can extrude toward the sternum lifting the skin and/or muscle/connective tissues from the breast bone merging the breasts together to form a connected mass. In fact the term synmastia means 'one breast'.

The synmastia complication may occur at the time of breast augmentation surgery, shortly after surgery or within a few months of the breast enhancement surgery. The better practice is to address the synmastia complication before it occurs where circumstances indicate it might be anticipated, and when not anticipated, to attempt a repair of the complication soon as it occurs. The reason is that if the condition is left unattended, the skin and connective tissues of the chest will be stretched, distorting breast and nipple/areola symmetry. Abnormal stretched breast skin and nipple deviations are usually very difficult to correct. Some women with long standing synmastia conditions necessarily elect to have the synmastia complication corrected without correction of associated nipple and areola distortions.

Correcting synmastia has typically involved a secondary breast surgery using several different techniques that depend on the woman's unique set of circumstances

SUMMARY OF THE INVENTION

A compression stabilizing, supporting and positioning bra for addressing and/or correcting synmastia complications in reconstructive breast surgeries includes a wide, cotton-lined, unidirectional elastic, torso band adjustably encircling the woman's thoracic torso immediately below the inframammary skinfold, a flared trapezoidal shaped, sternum compression panel secured at its base to the upper edge of the torso band below the inframammary skinfold and at the top, by a pair of adjustable shoulder straps for elastically compressing sternum tissues while restraining shaping and separating the inside conically rising, side portions of a woman's breasts, a pair of breast support cups/flaps also fastened to the upper edge of the torso band each secured at the top by an adjustable support strap, and elastic side panels fastened to the breast cup/flaps and the upper edge of the torso band for anchoring the respective shoulder straps of the sternum compression panel and breast cups/flaps supporting, restraining and shaping the outside, conical rising side portions of the woman's breasts.

DESCRIPTION OF PREFERRED AND EXEMPLARY EMBODIMENTS

Description of Figures and Images

DESCRIPTION OF PREFERRED AND EXEMPLARY EMBODIMENTS

Figure 1:
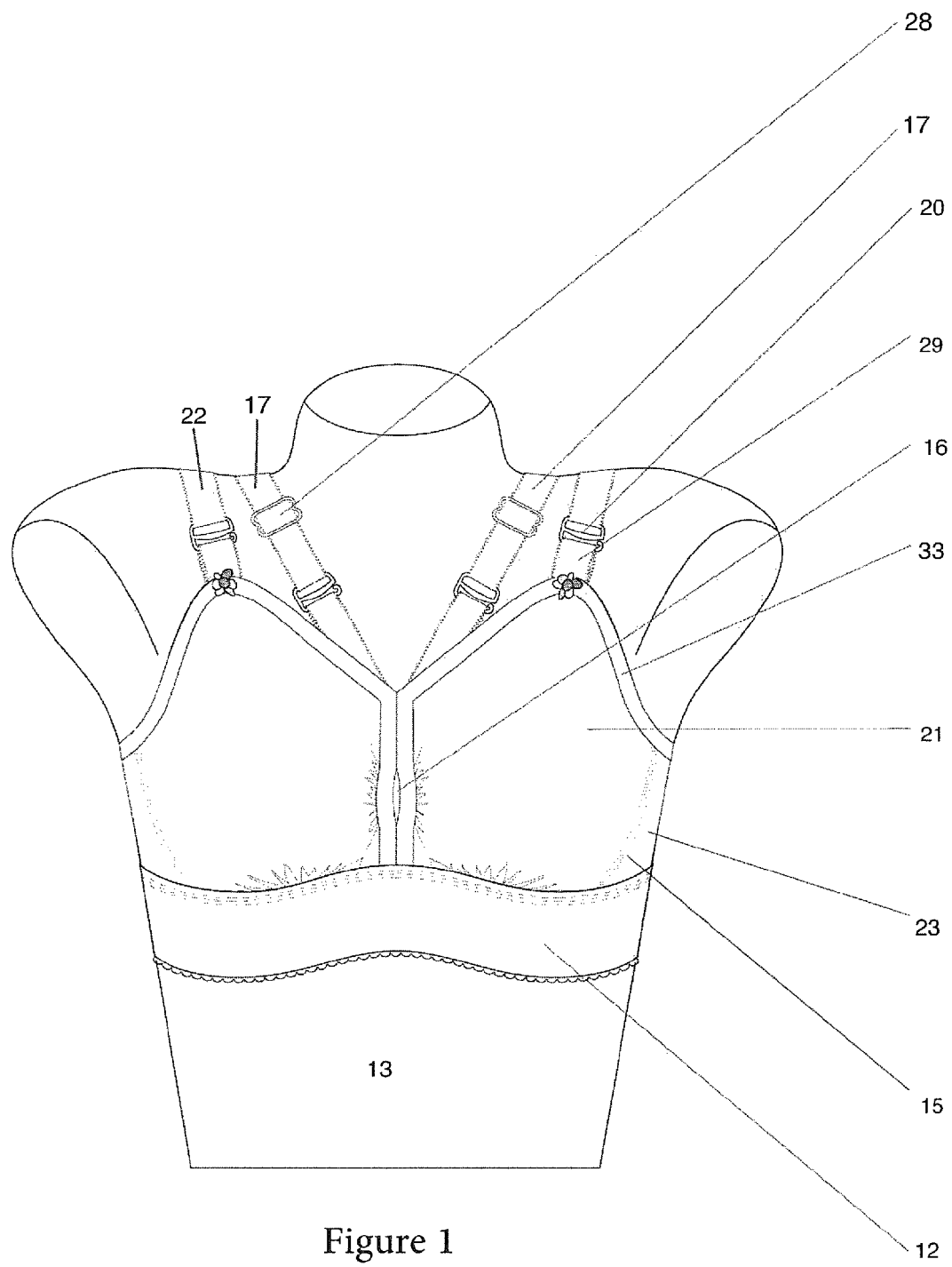
FIG. 1 shows the invented synmastia compression bra positioned on a female torso for applying compression for shaping and positioning a woman's breasts in a manner designed to preclude and/or correct a synmastia complication.
Figure 2:
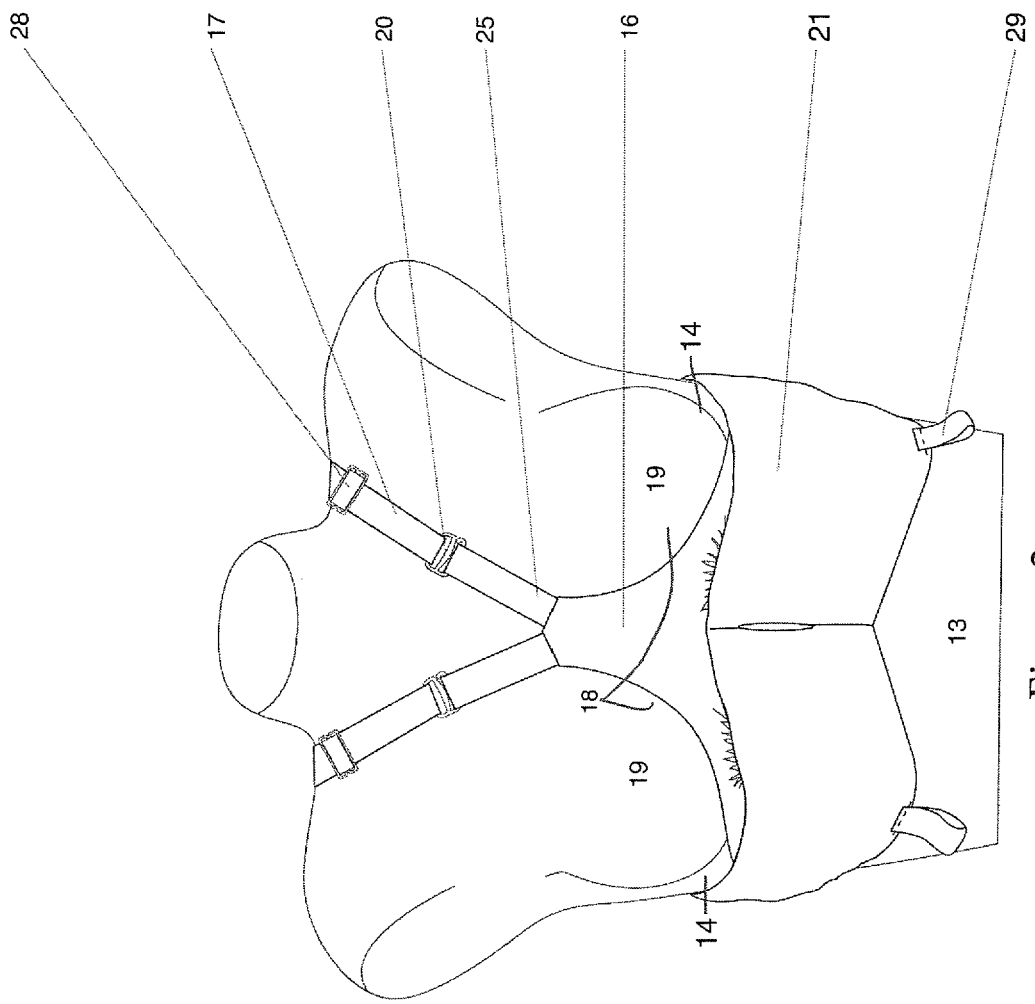
FIG. 2 shows the invented synmastia compression bra positioned on a female torso with the breast support cups/flaps undone hanging down illustrating the flaring trapezoidal shape sternum compression panel.
Figure 3:
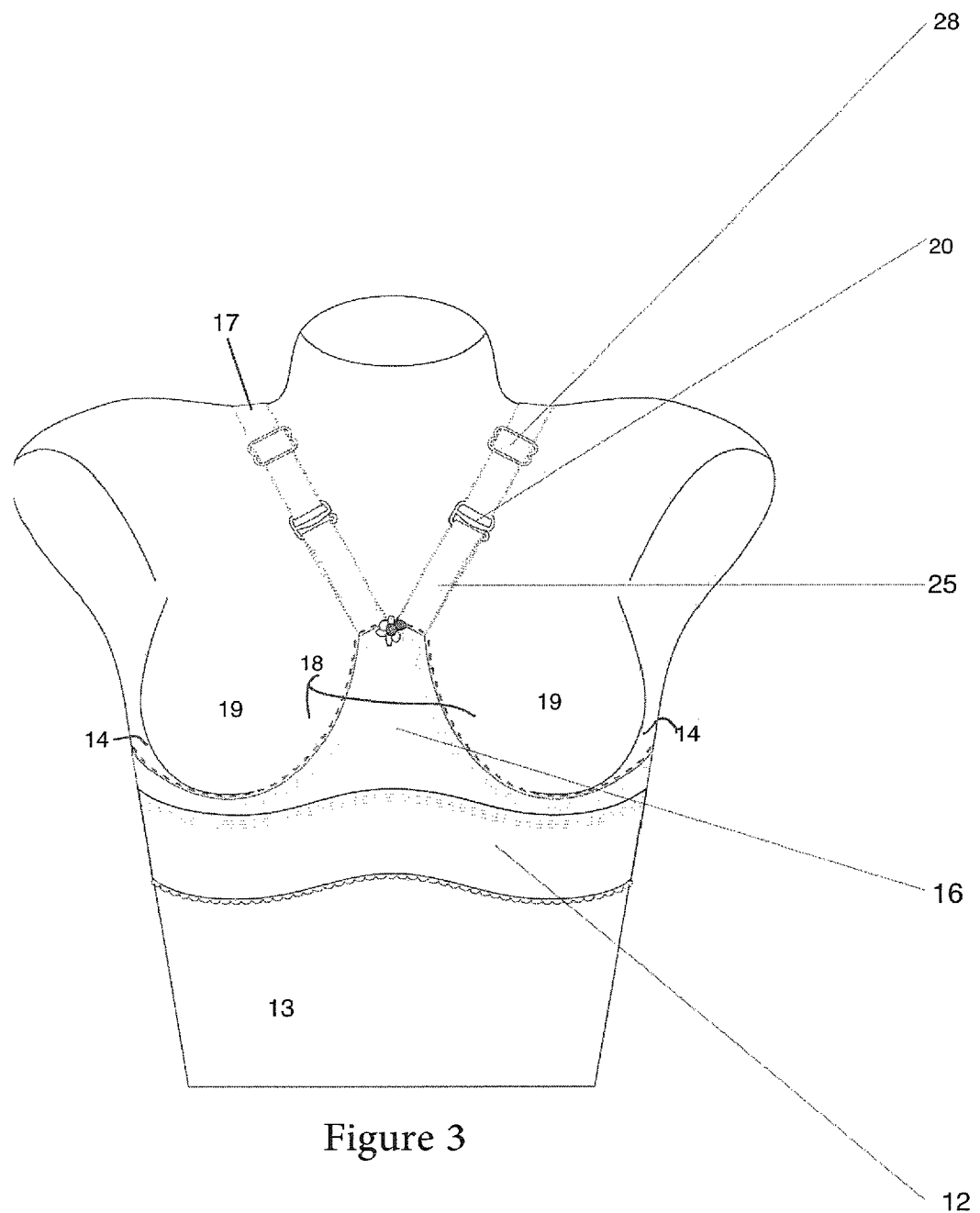
FIG. 3 illustrates the components of the bra that provides the compression precluding and/or correcting the synmastia complication.
Figure 4:
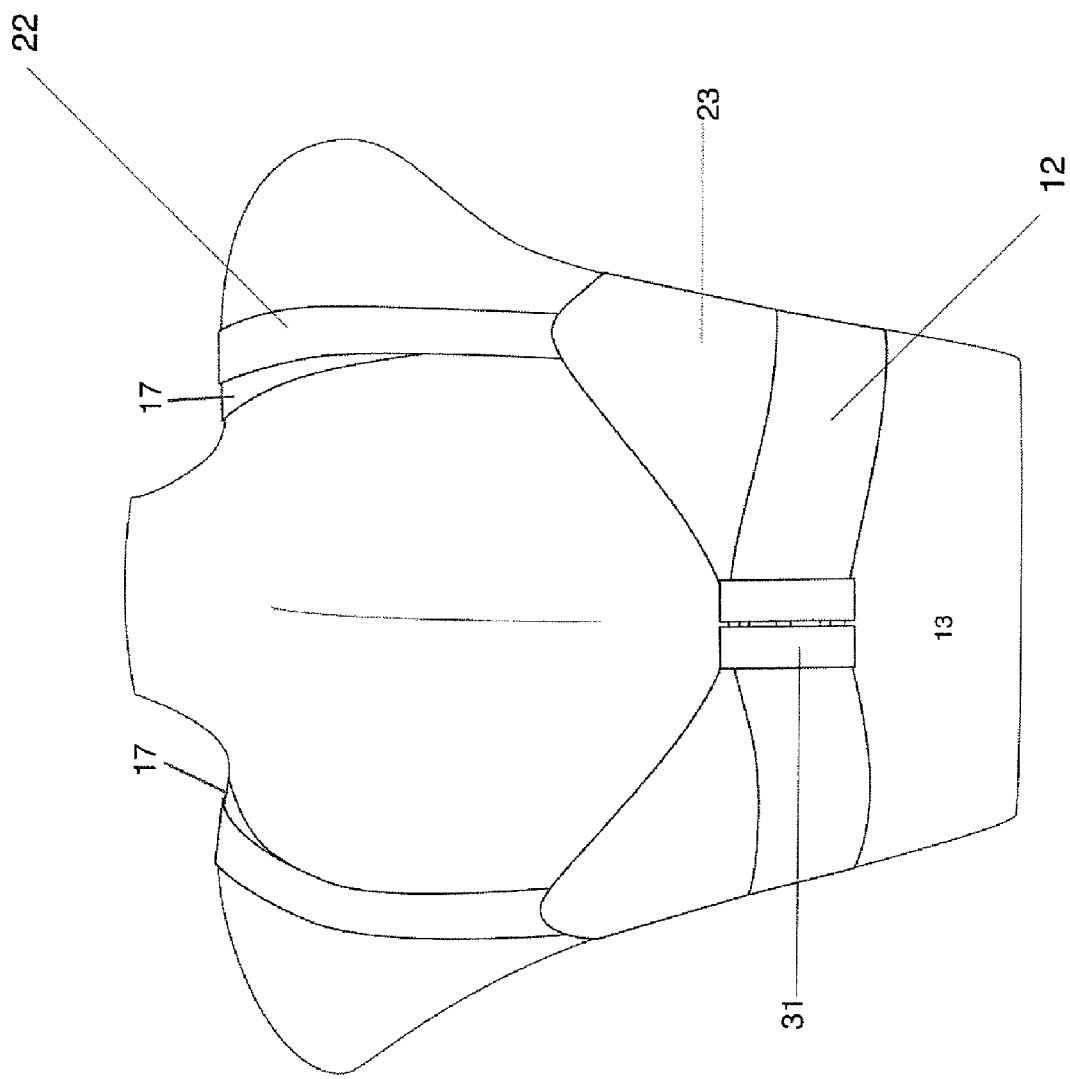
FIG. 4 shows a back view of the invented synmastia compression bra positioned on a female torso.
Figure 5:
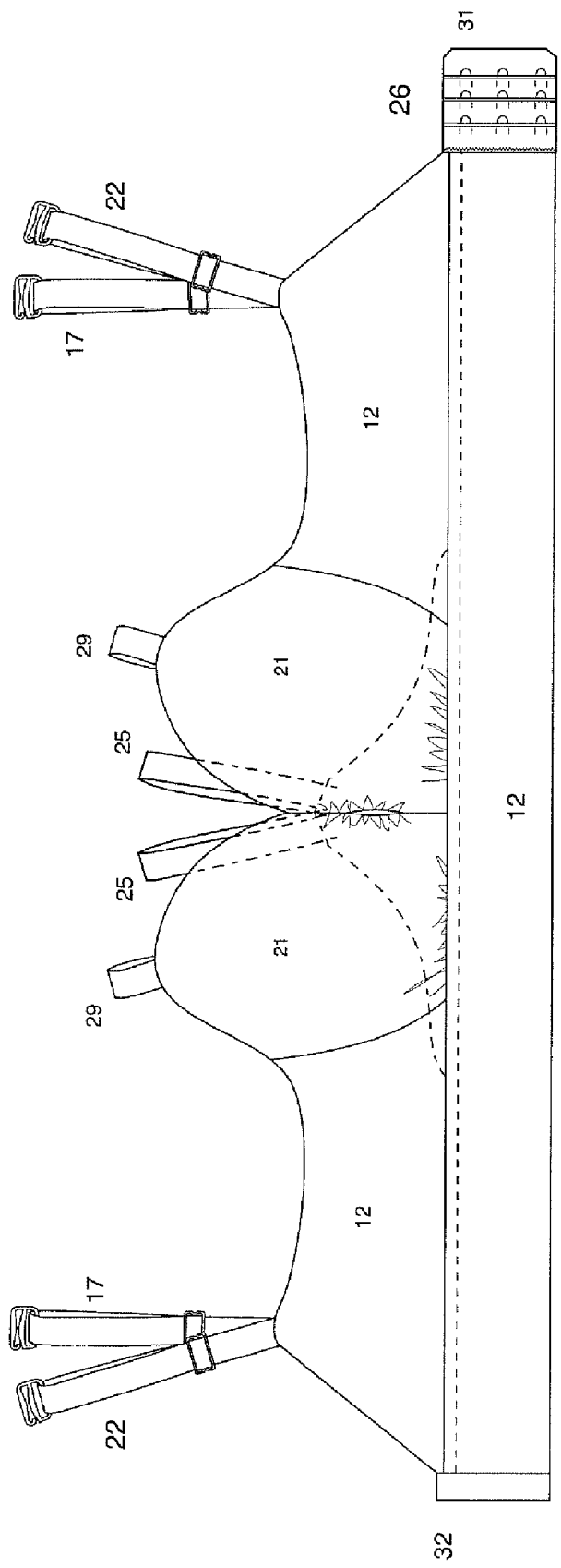
FIG. 5 shows a flat front or outside elevation view of the invented synmastia compression bra.
Figure 6:
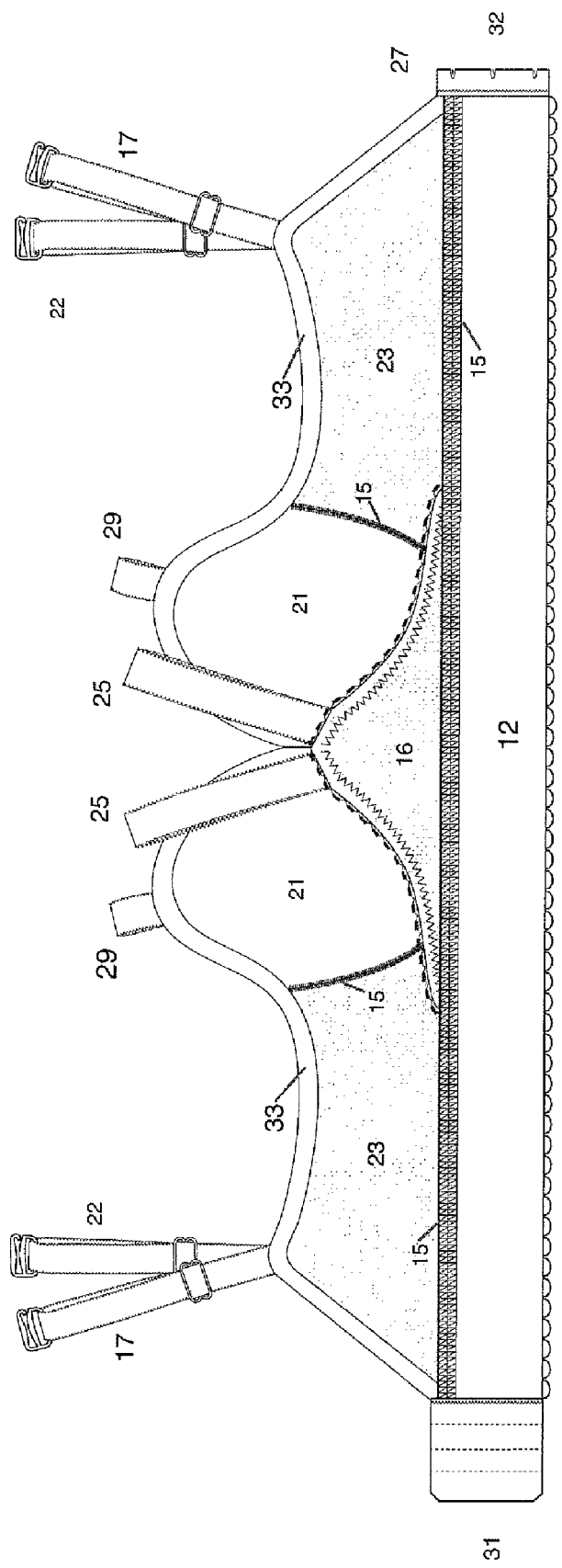
FIG. 6 shows a flat back or inside elevation view of the invented synmastia compression bra.

Looking at FIGS. 1-6, the synmastia compression bra includes a wide, unidirectional elastic torso band 12 for adjustably encircling a woman's thoracic torso 13 immediately below the inframammary skinfold 14. A flared, trapezoidal shaped, sternum compression panel 16 is secured at its base to the upper edge 15 of torso band 12 below the inframammary skinfold 14, and at its top by a pair of adjustable over-the-shoulder straps 17 for elastically compressing sternum tissues while restraining, shaping and separating the inside conically rising, side portions 18 of a woman's breasts 19. A pair of breast support cups/flaps 21 also fastened to the upper edge 15 of the torso band 12 each similarly secured at the top by an adjustable over-the-shoulder support strap 22.

Elastic side panels 23 fastened to the breast cup/flaps 22 and the upper edge 15 of the torso band 12 anchor the respective adjustable over-the-shoulder straps 17 & 22 of the sternum compression panel 16 and breast cups/flaps 21 supporting, restraining and shaping the outside, conical rising, side portions of the woman's breasts 19. The breast support cups/flaps 21 and elastic side panels include a spandex elastic band seam 33 folded over their top edges. The seams 15 joining the torso band 12 to the breast support cups/flaps 21, the elastic side panels 23 and the sternum compression panel 16 incorporate a spandex elastic bands as do the seams 15 joining the breast support cups/flaps 21 and the elastic side panels 23

The bra 11 is adjustably fastened together around the woman's torso 13 at the back, using three or more rows of eye fasteners 26 at the tab end 31 of the torso band 12 and a row of hook fasteners 27 at the other tab end 32 of the torso band 12. The over-the-shoulder straps 17 and 22 are adjusted using conventional adjustable sliders 28, and include conventional detachable hook closures 20 for hooking onto elastic loop straps 25 & 29 respectively fastened at the top of the trapezoidal shaped, sternum compression panel 16 and at the top of each breast cup/flap 21.

The physician and/or the patient sets the compression exerted by the a flared trapezoidal shaped, sternum compression panel 16 by adjusting the elastic tension of the over the shoulder straps 17 attaching the sternum compression panel 16 to the respective elastic side panels 23 on the back torso 13 of the patient.

The synmastia compression bra is fabricated from conventional elastic fabrics as specified in the above table referencing its components. The specific details disclosed herein should be interpreted as suggestions addressing design factors to be considered by those skilled in the art for creating preferred designs for such garments.

I claim:

1. A compression bra for addressing and/or correcting synmastia complications following reconstructive breast surgeries comprising in combination:
   (i) a wide, unidirectional elastic, torso band adjustably encircling a woman's thoracic torso with a top edge section located immediately below her inframammary skinfold;
   (ii) a curving, rising, trapezoidal shaped, elastic sternum compression panel secured along a straight base edge to the top edge section of the encircling torso band below the inframammary skinfold, and secured at a peak top edge section by a first pair of adjustable, over-the-shoulder, support straps straddling the woman's neck, for elastically compressing sternum tissues between the woman's breasts separating and preventing merger of her breasts across her sternum;
   (iii) a pair of breast support flaps for receiving, restraining and supporting the woman's breasts masses on her thoracic torso, having bottom edges adjacently secured along a central top edge section of the encircling torso

TABLE OF COMPONENTS AND MATERIALS

| Part Number | Name | Material |
|---|---|---|
|  | Synmastia Compression Bra | Various Spandex ® cotton elastic fabrics |
| 12 | Torso Band | 2 inch, inside cotton lined, unidirectional Spandex ® elastic band |
| 13 | Thoracic torso | Woman |
| 14 | Inframammary skinfold | Woman |
| 15 | Seams joining components of Bra | Conventional elastic seam stitches incorporating unidirectional Spandex ® elastic bands |
| 16 | Sternum Compression Panel | Double layer Spandex ® Power Knit Fabric |
| 17 | Adjustable shoulder straps for Compression Panel | Unidirectional elastic band |
| 18 | Inside rising surface of a breast | Woman |
| 19 | Woman's breast | Woman |
| 20 | hook closures | Conventional bra strap hooks |
| 21 | Breast cups/flaps | Cotton knit Spandex ® cups/panels |
| 22 | Adjustable shoulder straps for breast cups/flaps | Unidirectional Spandex ® elastic band |
| 23 | Elastic side panels | Double layer Spandex ® power knit fabric |
|  | Outside rising surface of a breast | Woman |
| 25 | Elastic Loop Closure Compression Panel | Unidirectional Spandex ® elastic band |
| 26 | Eye of fastener/coupling | Conventional Hook& Eye fastener/coupling |
| 27 | Hook of fastener coupling | Conventional Hook& Eye fastener/coupling |
| 28 | Adjustable Sliders for Shoulder strap | Bra Strap sliders |
| 29 | Elastic Loop Closure Breast cups/flaps | Unidirectional Spandex ® elastic band |
| 30 | Reserved |  |
| 31 | Hook fastener tab end of torso band | Inelastic Cotton Fabric |
| 32 | Eye fastener tab end of Torso Band | Inelastic Cotton Fabric |
| 33 | Fold over Elastic Band Seams | Conventional elastic seam stitches incorporating unidirectional Spandex ® elastic band | band below the breasts, joined sternum side edges, outside edges, and separate, conically tapering top edge sections;

(iv) a second pair of adjustable over-the-shoulder, support straps straddling the woman's neck each secured at one end to one of the top edge sections of the breast support flaps for adjusting restraint and support of the woman's breasts received within the breast support flaps on her thoracic torso; and (v) a pair of elastic side and back panels for supporting, restraining and shaping the outside, conical rising, side portions of the woman's breasts, each panel having a side edge fastened to one of the outside edges of the breast flaps, a bottom edge secured along the upper edge of opposite side and back sections of the encircling torso band, and a rising curved, back top, edge section adapted for, and anchoring ends of the respective first and second pairs of adjustable, over-the-shoulder support straps on corresponding sides of the woman's neck.

2. A compression bra for addressing and/or correcting synmastia complications following reconstructive breast surgeries, comprising in combination:

(i) a wide, unidirectional elastic, torso band adjustably encircling a woman's thoracic torso with an upper, front edge section located immediately below and conforming to her inframammary skinfolds, (ii) a curved, rising, trapezoidal shaped, elastic, sternum compression panel adapted for anchoring straps at its top, and secured along a straight base edge to the upper, front edge section of the encircling torso band, (iii) a first pair of adjustable, over-the-shoulder, support straps anchored to the sternum compression panel extending over the woman's shoulders straddling her neck, and separately fastened, to symmetrically spaced, separate back sections of the encircling torso band, for elastically compressing sternum tissues between a woman's breasts, separating and preventing merger of the woman's respective breasts across her sternum.

3. The compression bra of claim 2 and further including:

(iv) a symmetrical pair of elastic side and back panels each having a bottom edges secured along the upper edge of opposite side and back sections of the encircling torso band, and rising, curved upper back edge sections adapted for securing a plurality of adjustable, over-the-shoulder support straps extending over the woman's shoulder on either side of her neck, wherein the first pair of adjustable, over-the-shoulder, support straps are secured between the sternum compression panel and the curved, upper, back edge sections of the elastic side and back panels straddling the woman's neck.

4. The compression bra of claim 3 and further including:

(v) a pair of exterior breast support cups for receiving, restraining and supporting the woman's breasts with bottom edges adjacently secured along a central front section of the upper edge section of the encircling torso band beneath the woman's breasts, with joined inner sternum edges, with exterior side edges each secured to a side edge section of one of the elastic side and back panels, and with separate, conical, top edge sections adapted to anchor adjustable, over-the shoulder, support straps; and (vi) a second pair of adjustable over-the-shoulder, support straps each secured between a conical, top edge section of an exterior breast support cup, and the rising, curved, upper, back edge section of the elastic side and back panel on a corresponding side of the woman's neck, for adjustably restraining and supporting the woman's breasts on her thoracic torso.

* * * * *